(12) United States Patent
Audousset et al.

(10) Patent No.: US 7,972,387 B2
(45) Date of Patent: Jul. 5, 2011

(54) COMPOSITION FOR DYEING KERATIN FIBERS COMPRISING AT LEAST ONE OXIDATION BASE AND A POLYOXYETHYLENATED SORBITAN ESTER

(75) Inventors: Marie-Pascale Audousset, Asnieres (FR); Christine Rondeau, Sartrouville (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 11/502,398

(22) Filed: Aug. 11, 2006

(65) Prior Publication Data

US 2007/0079451 A1 Apr. 12, 2007

Related U.S. Application Data

(60) Provisional application No. 60/786,018, filed on Mar. 27, 2006.

(30) Foreign Application Priority Data

Aug. 11, 2005 (FR) ..................................... 05 52492

(51) Int. Cl.
*A61Q 5/10* (2006.01)
(52) U.S. Cl. ............. 8/405; 8/406; 8/410; 8/411; 8/421; 8/435; 8/580
(58) Field of Classification Search .............. 8/405, 406, 8/410, 411, 421, 435, 580
See application file for complete search history.

(56) References Cited

U.S. PATENT DOCUMENTS

| | | | |
|---|---|---|---|
| 4,003,699 A | 1/1977 | Rose et al. | |
| RE30,199 E | 1/1980 | Rose et al. | |
| 5,061,289 A | 10/1991 | Clausen et al. | |
| 5,380,340 A | 1/1995 | Neunhoeffer et al. | |
| 5,534,267 A | 7/1996 | Neunhoeffer et al. | |
| 5,663,366 A | 9/1997 | Neunhoeffer et al. | |
| 5,766,576 A | 6/1998 | Lowe et al. | |
| 6,099,592 A | 8/2000 | Vidal et al. | |
| 6,099,593 A | 8/2000 | Terranova et al. | |
| 6,284,003 B1 * | 9/2001 | Rose et al. | 8/412 |
| 6,338,741 B1 | 1/2002 | Vidal et al. | |
| 6,730,789 B1 | 5/2004 | Birault et al. | |
| 2002/0050013 A1 | 5/2002 | Vidal et al. | |
| 2003/0019051 A9 | 1/2003 | Vidal et al. | |

FOREIGN PATENT DOCUMENTS

| | | |
|---|---|---|
| DE | 23 59 399 | 6/1975 |
| DE | 38 43 892 A1 | 6/1990 |
| DE | 41 33 957 A1 | 4/1993 |
| DE | 195 43 988 A1 | 5/1997 |
| DE | 199 23 438 A1 | 11/2000 |
| EP | 0 770 375 B1 | 5/1997 |
| FR | 2 733 749 A1 | 11/1996 |
| FR | 2 750 048 A1 | 12/1997 |
| FR | 2 801 308 A1 | 5/2001 |
| GB | 1 026 978 | 4/1966 |
| GB | 1 153 196 | 5/1969 |
| JP | 2-19576 | 1/1990 |
| WO | WO 94/08969 | 4/1994 |
| WO | WO 94/08970 | 4/1994 |
| WO | WO 96/15765 | 5/1996 |
| WO | WO 2004/093835 A1 | 11/2004 |

OTHER PUBLICATIONS

Patent Abstract of Japan 03 157320 A (May 1991).*
Hydrophobic Oxidative Hair Dye—XP-002380394 (Feb. 2002).*
Patent Abstracts of Japan, vol. 15, No. 388, Oct. 2, 1991, JP 03 157320 A.
"Hydrophobic Oxidative Hair Dye 8781-58," Haircareformulation. Com, Feb. 11, 2002, XP-002380394.
English language abstract of DE 199 23 438 A1, Nov. 30, 2000.
French Search Report for FR 0552492, dated May 11, 2006.
French Search Report for FR 0552494, dated May 10, 2006, Examiner E. Siatou, for co-pending patent application Attorney Docket No. 05725.1606-00000, filed Aug. 11, 2006.
Co-pending Patent Application—Title: Process for Coloring Keratin Fibers Comprising Treating the Scalp With at Least One Sorbitan Ester Filed: Aug. 11, 2006.
English language abstract of EP 0 770 375 B1, May 2, 1997.
English language abstract of JP 2-19576, Jan. 23, 1990.

* cited by examiner

*Primary Examiner* — Eisa B Elhilo
(74) *Attorney, Agent, or Firm* — Finnegan, Henderson, Farabow, Garrett & Dunner, LLP

(57) ABSTRACT

The present disclosure relates to a composition for dyeing keratin fibers such as the hair, which comprises, in a suitable medium, at least one oxidation base, optionally at least one coupler and at least one polyoxyethylenated sorbitan ester with a number of moles of ethylene oxide of less than or equal to 10. Such a composition makes it possible to conserve a strong coloration, while at the same time limiting the discomfort that may be experienced on the scalp at the time of application of the dye composition or after this application.

11 Claims, No Drawings

COMPOSITION FOR DYEING KERATIN FIBERS COMPRISING AT LEAST ONE OXIDATION BASE AND A POLYOXYETHYLENATED SORBITAN ESTER

This application claims benefit of U.S. Provisional Application No. 60/786,018, filed Mar. 27, 2006, the contents of which are incorporated herein by reference. This application also claims benefit of priority under 35 U.S.C. §119 to French Patent Application No. FR 05 52492, filed Aug. 11, 2005, the contents of which are also incorporated herein by reference.

The present disclosure relates to a composition for dyeing keratin fibers, which comprises at least one oxidation base and a polyoxyethylenated sorbitan ester.

It is known practice to dye keratin fibers, including human hair, with dye compositions containing oxidation dye precursors, which are generally known as oxidation bases, such as ortho- or para-phenylenediamines, ortho- or para-aminophenols and heterocyclic compounds. These oxidation bases are colorless or weakly colored compounds, which, when combined with oxidizing products, can give rise to colored compounds via a process of oxidative condensation. The shades obtained with these oxidation bases can be modified by adding couplers or coloration modifiers, the latter being chosen, for example, from aromatic meta-diaminobenzenes, meta-aminophenols, meta-diphenols and certain heterocyclic compounds such as indole and pyridine compounds.

Oxidation dyeing is generally performed in the presence of an alkaline agent that promotes the dyeing of keratin fibers.

The variety of molecules used as oxidation bases and couplers allows a wide range of colors to be obtained. The "permanent" coloration obtained by means of these oxidation dyes makes it possible to obtain shades in the desired intensity and shows good fastness with respect to external agents such as light, bad weather, washing, permanent waving, perspiration and rubbing.

However, since oxidation dyeing is performed in the presence of an oxidizing agent and an alkaline agent, it occasionally leads to a sensation of discomfort reflected by local stinging and/or heating of the scalp.

It is already known practice to protect keratin fibers that need to undergo or that have undergone a coloration using a dye precursor, for example, by using particular polymers. However, this protection is not entirely satisfactory. It may lead to less powerful dyeing due to the presence of these polymers.

Moreover, it is already known practice to use polyoxyethylenated sorbitan esters in keratin fiber dyeing products. For example, German Patent Application No. DE 199 23 438 describes the use of polyoxyethylenated sorbitan esters to reduce the staining of the scalp during dyeing.

A first aspect of the present disclosure thus relates to a novel composition for dyeing keratin fibers such as the hair, which makes it possible to limit the discomfort that may be experienced by the user during dyeing.

The present disclosure also relates to a composition for dyeing keratin fibers such as the hair, which comprises, in a suitable medium, at least one oxidation base, optionally at least one coupler and at least one polyoxyethylenated sorbitan ester with a number of moles of ethylene oxide of less than or equal to 10.

Such a composition can conserve a strong coloration, while at the same time limiting the discomfort that may be experienced on the scalp at the time of application of the dye composition or after this application.

Oxidation bases that can be used in the composition of the present disclosure are the oxidation bases conventionally used for oxidation dyeing.

Oxidation bases may be chosen, for example, from para-phenylenediamines, bis(phenyl)alkylenediamines, para-aminophenols, bis-para-aminophenols, ortho-aminophenols and heterocyclic bases, and the addition salts thereof.

Among the para-phenylenediamines that may be used according to the present disclosure, non-limiting mention may be made of para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid.

Among the para-phenylenediamines mentioned above para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid are used in at least one embodiment of the present disclosure.

Among the bis(phenyl)alkylenediamines that may be used according to the present disclosure, non-limiting mention may be made, for example, of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof with an acid.

Among the para-aminophenols that may be used according to the present disclosure, non-limiting mention may be made, for example, of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be used according to the present disclosure, non-limiting mention may be made, for example, of 2-aminophenol, 2-amino-5-methylphenol, 2-amino-6-methylphenol and 5-acetamido-2-aminophenol, and the addition salts thereof with an acid.

Among the heterocyclic bases that may be used according to the present disclosure, non-limiting mention may be made, for example, of pyridine derivatives, pyrimidine derivatives and pyrazole derivatives such as 4,5-diaminopyrazole derivatives.

Among the pyridine derivatives which may be used according to the present disclosure, non-limiting mention may be made of the compounds described, for example, in British Patent Nos. GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the addition salts thereof with an acid.

Other pyridine oxidation bases that may be used according to the present disclosure include the 3-aminopyrazolo[1,5-a]pyridine oxidation bases or the addition salts thereof described, for example, in French Patent Application No. FR 2 801 308. By way of example, non-limiting mention may be made of pyrazolo[1,5-a]pyrid-3-ylamine; 2-acetylaminopyrazolo[1,5-a]pyrid-3-ylamine; 2-morpholin-4-ylpyrazolo[1,5-a]pyrid-3-ylamine; 3-aminopyrazolo[1,5-a]pyridine-2-carboxylic acid, 2-methoxypyrazolo[1,5-a]pyrid-3-ylamine; (3-aminopyrazolo[1,5-a]pyrid-7-yl)methanol; 2-(3-aminopyrazolo[1,5-a]pyrid-5-yl) ethanol; 2-(3-aminopyrazolo[1,5-a]pyrid-7-yl)ethanol; (3-aminopyrazolo[1,5-a]pyrid-2-yl) methanol; 3,6-diaminopyrazolo[1,5-a]pyridine; 3,4-diaminopyrazolo[1,5-a]pyridine; pyrazolo[1,5-a]pyridine-3,7-diamine; 7-morpholin-4-ylpyrazolo[1,5-a]pyrid-3-ylamine; pyrazolo[1,5-a]pyridine-3,5-diamine; 5-morpholin-4-ylpyrazolo[1,5-a]pyrid-3-ylamine; 2-[(3-aminopyrazolo[1,5-a]pyrid-5-yl)(2-hydroxyethyl)amino]ethanol; 2-[(3-aminopyrazolo[1,5-a]pyrid-7-yl)(2-hydroxyethyl)amino]ethanol; 3-aminopyrazolo[1,5-a]pyrid-5-ol; 3-aminopyrazolo[1,5-a]pyrid-4-ol; 3-aminopyrazolo[1,5-a]pyrid-6-ol; 3-aminopyrazolo[1,5-a]pyrid-7-ol; and also the addition salts thereof with an acid or with a base.

Among the pyrimidine derivatives which may be used according to the present disclosure, non-limiting mention may be made of the compounds described, for example, in, German Patent No. DE 2 359 399; Japanese Patent Nos. JP 88-169571 and JP 05-63124; European Patent No. EP 0 770 375; or International Patent Application No. WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in French Patent Application No. FR-A-2 750 048 and among which non-limiting mention may be made, for example, of pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl) (2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine and 3-amino-5-methyl-7-imidazolylpropylaminopyrazolo[1,5-a]pyrimidine, and the addition salts thereof with an acid and the tautomeric forms thereof, when a tautomeric equilibrium exists.

Among the pyrazole derivatives which may be used according to the present disclosure, non-limiting mention may be made of the compounds described in German Patent Nos. DE 3 843 892 and DE 4 133 957; International Patent Application Nos. WO 94/08969 and WO 94/08970; French Patent Application No. FR-A-2 733 749; and German Patent Application No. DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof with an acid.

The compositions according to at least one embodiment of the present disclosure contain at least one para-phenylenediamine and/or at least one para-aminophenol.

The at least one oxidation base present in the dye composition of the present disclosure is individually present in an amount ranging from 0.001% to 10% by weight, relative to the total weight of the dye composition, such as, for example, from 0.005% to 6% by weight, relative to the total weight of the dye composition.

The composition of the present disclosure may contain at least one coupler. The at least one coupler can be chosen from couplers conventionally used in the context of oxidation dyeing, such as meta-phenylenediamine couplers, meta-aminophenol couplers, meta-diphenol couplers, naphthalene-based couplers and heterocyclic couplers, and the addition salts thereof.

Examples of couplers that may be used according to the present disclosure, non-limiting mention may be made of 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene and 2,6-bis(β-hydroxyethylamino)toluene, and the addition salts thereof with an acid.

In the dye composition of the present disclosure, the at least one coupler, when they are present, is individually present in an amount ranging from 0.001% to 10% by weight, such as, for example, from 0.005% to 6% by weight, relative to the total weight of the dye composition.

As examples of polyoxyethylenated sorbitan esters with a number of moles of ethylene oxide of less than or equal to 10, non-limiting mention may be made of sorbitan monolaurate oxyethylenated with 4 EO or polysorbate 21, sorbitan monostearate oxyethylenated with 4 EO or polysorbate 61, and sorbitan monooleate oxyethylenated with 5 EO or polysorbate 81. These sorbitan esters are sold, for example, by the company Uniqema under the name Tween 21, Tween 61 or Tween 81.

According to at least one embodiment, the number of moles of ethylene oxide is less than 6 mol of ethylene oxide, and, for example, may range from 2 to 5 mol of ethylene oxide, limits inclusive.

According to the present disclosure, the sorbitan ester may be present in the composition in a very variable amount that depends, for example, on the type of coloration or the nature of the keratin fibers to be dyed. According to at least one embodiment, the composition may contain an amount of sorbitan ester ranging from 0.01% to 20% by weight, such as, for example, from 0.1% to 10% or from 1% to 8% by weight, relative to the total weight of the composition.

The dye composition may also comprise direct dyes. Among examples of direct dyes that may be used according to the present disclosure, non-limiting mention may be made of neutral, acidic or cationic nitrobenzene direct dyes, neutral, acidic or cationic azo direct dyes, neutral, acidic or cationic quinone and, as further examples, anthraquinone direct dyes, azine direct dyes, triarylmethane direct dyes, indoamine direct dyes and natural direct dyes.

In at least one embodiment, the medium that is suitable for dyeing is a cosmetic medium comprising water or a mixture of water and at least one organic solvent, for instance branched or unbranched $C_1$-$C_4$ lower alcohols, such as ethanol and isopropanol; polyols and polyol ethers such as 2-butoxyethanol, propylene glycol, propylene glycol monomethyl ether, diethylene glycol monoethyl ether and monomethyl ether, and glycerol, and also aromatic alcohols such as benzyl alcohol or phenoxyethanol, and mixtures thereof.

According to at least one embodiment, the at least one solvent is present in an amount ranging from 1% to 40% by weight, such as, for example, from 5% to 30% by weight, relative to the total weight of the dye composition.

The dye composition that is useful in the process of the disclosure may also contain at least one adjuvant conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, penetrants, sequestrants, fragrances, buffers, dispersants, conditioning agents, for instance volatile or non-volatile, modified or unmodified silicones, film-forming agents and, for example, nonionic, cationic, anionic or amphoteric fixing polymers, preserving agents and opacifiers.

According to at least one embodiment, the composition of the present disclosure contains at least one surfactant, such as, for example, a nonionic surfactant, and/or a thickening polymer.

In at least one embodiment of the present disclosure, the at least one adjuvant is individually present in an amount ranging from 0.01% to 20% by weight relative to the weight of the composition.

Needless to say, a person skilled in the art will take care to select this or these optional additional compounds such that the advantageous properties intrinsically associated with the composition in accordance with the present disclosure are not, or are not substantially, adversely affected by the addition(s) envisaged.

The pH of the dye composition in accordance with at least one embodiment of the present disclosure ranges from 2 to 12, such as, for example, from 6 to 12.

The pH may be adjusted to the desired value using acidifying or basifying agents usually used in the dyeing of keratin fibers, or alternatively using standard buffer systems.

Among the acidifying agents that may be used according to the present disclosure, non-limiting mention may be made, for example, of mineral or organic acids such as hydrochloric acid, orthophosphoric acid, sulfuric acid, carboxylic acids such as acetic acid, tartaric acid, citric acid and lactic acid, and sulfonic acids.

Among the basifying agents that may be used according to the present disclosure, non-limiting mention may be made, for example, of aqueous ammonia, alkaline carbonates, alkanolamines such as mono-, di- and triethanolamine and derivatives thereof, sodium hydroxide, potassium hydroxide and the compounds of formula (III) below:

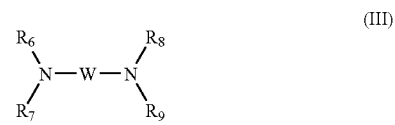

(III)

wherein:
W is chosen from propylene residues that are unsubstituted or substituted with a hydroxyl group or a $C_1$-$C_4$ alkyl radical; and
$R_6$, $R_7$, $R_8$ and $R_9$, which may be identical or different, are chosen from hydrogen atoms, $C_1$-$C_4$ alkyl radicals and $C_1$-$C_4$ hydroxyalkyl radicals.

In at least one embodiment of the present disclosure, the dye composition used comprises a composition containing an alkaline agent, this alkaline agent being present in an amount of greater than 5% by weight relative to the weight of the dye composition. In at least one embodiment, the alkaline agent may be present in amounts of greater than 10%, such as greater than 15%.

According to at least one embodiment of the present disclosure, the dye composition comprises or is intended to be used with at least one basifying agent, such as, for example, ammonia and/or an alkanolamine such as ethanolamine and/or a silicate such as sodium silicate.

The dye composition according to the present disclosure may be in various forms, such as in the form of liquids, creams or gels, or in any other form that is suitable for dyeing keratin fibers, including human hair.

The dye composition may also comprise an oxidizing agent. Oxidizing agents conventionally used for the oxidation dyeing of keratin fibers include, for example, hydrogen peroxide, urea peroxide, alkali metal bromates, persalts such as perborates and persulfates, peracids and oxidase enzymes, among which non-limiting mention may be made of peroxidases, 2-electron oxidoreductases such as uricases and 4-electron oxygenases such as laccases. Hydrogen peroxide is used as an oxidizing agent in at least one embodiment.

The oxidizing agent may be added to the dye composition just at the time of use, or it may be already be included in the dye composition, this composition being applied simultaneously with or sequentially to the composition of the disclosure. The oxidizing composition may also contain various adjuvants conventionally used in hair dye compositions and as defined above.

In at least one embodiment, the pH of the oxidizing composition containing the oxidizing agent is such that, after mixing with the dye composition, the pH of the resulting composition applied to the keratin fibers ranges from 3 to 12, such as, for example, from 6 to 12. It may be adjusted to the desired value by means of acidifying or basifying agents usually used in the dyeing of keratin fibers and as defined above.

The dye composition that is finally applied to the keratin fibers may be in various forms, such as in the form of liquids, creams or gels or in any other form that is suitable for dyeing keratin fibers, including human hair.

The dyeing of keratin fibers is performed conventionally by applying the dye composition for a time that is sufficient to obtain the desired coloration. In at least one embodiment, the leave-on time ranges from 1 to 60 minutes, such as, for example, from 5 to 60 minutes. This dyeing step may be followed by a rinsing step.

The dyeing step may be performed at room temperature or at higher temperatures, for example using a hairdryer, a drying hood, a smoothing iron, or any other art recognized method for increasing the temperature.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding the numerical ranges and parameters setting forth the broad scope of the invention as approximations, the numerical values set forth in the specific examples are reported as precisely as possible. Any numerical value, however, inherently contains certain errors necessarily resulting from the standard deviation found in its respective testing measurement.

The examples that follow are intended to illustrate the invention. The invention is not, however, limited to these embodiments.

EXAMPLES

The dye composition below was prepared (in grams):

|  | Example 1 | Example 2 |
|---|---|---|
| 1-Methyl-2,5-diaminobenzene | 1.7 g | 0.5 g |
| 1-Hydroxy-4-aminobenzene |  | 0.4 g |
| 1,3-Dihydroxybenzene | 1 g | 0.25 g |
| 1-Hydroxy-3-aminobenzene | 0.07 g |  |
| 1-β-Hydroxyethyloxy-2,4-diaminobenzene dihydrochloride | 0.03 g |  |
| 2-Methyl-1,3-dihydroxybenzene | 0.5 g | 0.3 g |
| 1-Methyl-2-hydroxy-4-aminobenzene |  | 0.25 g |
| 1-Methyl-2-hydroxy-4-β-hydroxyethylaminobenzene |  | 0.05 g |
| 6-Hydroxyindole |  | 0.01 g |
| Pure monoethanolamine | 5 g |  |
| Aqueous ammonia containing 20% $NH_3$ |  | 10 g |
| Polyquaternium-6 sold by Nalco |  | 3 g |
| Polyquaternium-22 sold by Nalco | 1.5 g |  |
| Hexadimethrine chloride (Mexomere PO, Chimex) | 1.5 g |  |
| Propylene glycol | 10 g | 10 g |
| Carbopol 980 sold by Noveon (crosslinked polyacrylic acid) | 0.4 g | 0.4 g |
| Lauryl alcohol oxyethylenated with 12 mol of ethylene oxide | 7.5 g | 7.5 g |
| Oleocetyl alcohol oxyethylenated with 30 mol of EO | 6 g | 6 g |
| Decyl alcohol oxyethylenated with 3 mol of EO | 8 g | 8 g |
| Lauric acid | 2.5 g | 2.5 g |
| 50/50 Cetylstearyl alcohol | 10 g | 10 g |
| Hydrophobic fumed silica | 1 g | 1 g |
| Glyceryl monostearate | 1 g | 1 g |
| Sorbitan monolaurate oxyethylenated with 4 EO | 3 g | 5 g |
| Reducing agent, antioxidant, sequestrant, fragrance | qs | qs |
| Demineralized water qs | 100 g | 100 g |

|  | Example 3 | Example 4 |
|---|---|---|
| 1-Methyl-2,5-diaminobenzene | 1.7 g | 0.007 g |
| 1-Hydroxy-4-aminobenzene |  | 0.007 g |
| 1,3-Dihydroxybenzene | 1 g | 0.014 g |
| 1-Hydroxy-3-aminobenzene | 0.07 g |  |
| 1-β-Hydroxyethyloxy-2,4-diaminobenzene dihydrochloride | 0.03 g |  |
| 2-Methyl-1,3-dihydroxybenzene | 0.5 g |  |
| Aqueous ammonia containing 20% $NH_3$ | 10 g | 20 g |
| Polyquaternium-6 sold by Nalco |  | 3 g % |
| Polyquaternium-22 sold by Nalco | 1.5 g |  |
| Hexadimethrine chloride (Mexomere PO, Chimex) | 1.5 g |  |
| Oleic acid | 2.5 g | 2.5 g |
| Oxyethylenated fatty alcohols | 15 g | 15 g |
| Oleyl alcohol | 1 g | 1 g |
| Monamid 972 sold by Uniqema (fatty amide) | 3 g | 5 g |
| Glycerol |  | 5 g |
| Polyurethane-16 | 0.2 g | 0.4 g |
| Hydroxypropylmethylcellulose | 0.3 g | 0.7 g |
| Sorbitan monolaurate oxyethylenated with 4 EO | 5 g | 7 g |
| Reducing agent, antioxidant, sequestrant, fragrance | qs | qs |
| Demineralized water qs | 100 g | 100 g |

Composition 1 was mixed extemporaneously with one and a half times its volume of 9-volumes aqueous hydrogen peroxide solution (pH in the region of 3).

Composition 2 was mixed extemporaneously with one and a half times its volume of 20-volumes aqueous hydrogen peroxide solution.

Composition 3 was mixed extemporaneously with one and a half times its volume of 20-volumes aqueous hydrogen peroxide solution (pH in the region of 3).

Composition 4 was mixed extemporaneously with twice its volume of 40-volumes aqueous hydrogen peroxide solution (pH in the region of 3).

Each mixture thus obtained was applied to grey hair containing 90% white hairs, at a rate of 30 g per 3 g of hair. The leave-on time at room temperature was 20 minutes for compositions 1 and 2 and 30 minutes for compositions 3 and 4.

The hair was then rinsed, washed with a standard shampoo and dried. The hair coloration was evaluated visually.

|  | Tone depth | Tint |
|---|---|---|
| Composition 1 | Chestnut | Natural |
| Composition 2 | Dark blond | Mahogany coppery |
| Composition 3 | Chestnut | Natural |
| Composition 4 | Very, very light blond | Natural |

The fibers thus obtained showed a satisfactory coloration under comfortable conditions for the model.

What is claimed is:

1. A composition for dyeing keratin fibers, comprising, in a suitable medium:
   at least one oxidation base,
   at least one coupler, and
   at least one polyoxyethylenated sorbitan ester with a number of moles of ethylene oxide ranging from 2 to 5,
   wherein the at least one polyoxyethylenated sorbitan ester is present in an amount ranging from 1% to 8% by weight relative to the total weight of the composition; and
   wherein the at least one polyoxyethylenated sorbitan ester is chosen from sorbitan monolaurate oxyethylenated with 4 EO and sorbitan monostearate oxyethylenated with 4 EO.

2. The composition according to claim 1, wherein the at least one oxidation base is chosen from para-phenylenediamines, bis(phenyl)alkylenediamines, para-aminophenols, bis-para-aminophenols, ortho-aminophenols and heterocyclic bases, and the addition salts thereof.

3. The composition according to claim 2, wherein the at least one oxidation base is present in the dye composition individually in an amount ranging from 0.001% to 10% by weight relative to the total weight of the composition.

4. The composition according to claim 3, wherein the at least one oxidation base is present in the dye composition individually in an amount ranging from 0.005% to 6% by weight relative to the total weight of the composition.

5. The composition according to claim 1, further comprising at least one coupler chosen from meta-phenylenediamine couplers, meta-aminophenol couplers, meta-diphenol couplers, naphthalene-based couplers and heterocyclic couplers, and the addition salts thereof.

6. The composition according to claim 5, wherein the at least one coupler is individually present in an amount ranging from 0.001% to 10% by weight relative to the total weight of the dye composition.

7. The composition according to claim 6, wherein the at least one coupler is individually present in an amount ranging from 0.005% to 6% by weight relative to the total weight of the dye composition.

8. The composition according to claim 1, further comprising at least one direct dye.

9. The composition according to claim 1, further comprising at least one basifying agent.

10. A process for dyeing keratin fibers, comprising:
    applying a composition to the keratin fibers for a time that is sufficient to obtain the desired coloration, wherein the composition comprises, in a suitable medium:
    at least one oxidation base,
    at least one coupler, and
    at least one polyoxyethylenated sorbitan ester with a number of moles of ethylene oxide ranging from 2 to 5,
    wherein the at least one polyoxyethylenated sorbitan ester is present in an amount ranging from 1% to 8% by weight relative to the total weight of the composition; and
    wherein the at least one polyoxyethylenated sorbitan ester is chosen from sorbitan monolaurate oxyethylenated with 4 EO and sorbitan monostearate oxyethylenated with 4 EO.

11. A method for eliminating or reducing sensations of discomfort associated with applying a dye composition to the scalp in the presence of an oxidizing agent comprising applying a composition comprising, in a suitable medium:
    at least one polyoxyethylenated sorbitan ester with a number of moles of ethylene oxide ranging from 2 to 5,
    wherein the at least one polyoxyethylenated sorbitan ester is present in an amount ranging from 1% to 8% by weight relative to the total weight of the composition;
    wherein the at least one polyoxyethylenated sorbitan ester is chosen from sorbitan monolaurate oxyethylenated with 4 EO and sorbitan monostearate oxyethylenated with 4 EO;
    at least one coupler; and
    at least one oxidation base.

* * * * *